United States Patent
Ogawa et al.

(10) Patent No.: US 7,569,707 B2
(45) Date of Patent: Aug. 4, 2009

(54) PRODUCTION METHOD OF HIGHLY PURE PYROMELLITIC DIANHYDRIDE

(75) Inventors: Hiroshi Ogawa, Okayama (JP); Atsushi Okoshi, Okayama (JP); Masashi Yabuno, Okayama (JP); Masato Inari, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 564 days.

(21) Appl. No.: 11/490,126

(22) Filed: Jul. 21, 2006

(65) Prior Publication Data

US 2007/0021622 A1    Jan. 25, 2007

(30) Foreign Application Priority Data

Jul. 21, 2005   (JP) ............................. 2005-211630

(51) Int. Cl.
*C07D 493/04*   (2006.01)
(52) U.S. Cl. ..................................... 549/239
(58) Field of Classification Search ................... 549/239
See application file for complete search history.

(56) References Cited

FOREIGN PATENT DOCUMENTS

| EP | 1 439 161 | 7/2004 |
|---|---|---|
| GB | 1 112 817 | 5/1968 |
| GB | 1280562 | 7/1972 |
| JP | 62-59280 | 3/1987 |
| JP | 2000-1484 | 1/2000 |
| JP | 2001-59022 | 3/2001 |

OTHER PUBLICATIONS

European Search Report, for Application No. EP 06 11 7497, dated Nov. 23, 2006.

*Primary Examiner*—Bernard Dentz
(74) *Attorney, Agent, or Firm*—Antonelli, Terry, Stout & Kraus, LLP.

(57) ABSTRACT

A method of producing pyromellitic dianhydride. The method includes a step of heating a crude pyromellitic acid in the absence of acetic anhydride to convert a part of pyromellitic acid to pyromellitic anhydride, and a subsequent step of heating the resultant mixture in the presence of acetic anhydride to complete the anhydrization of pyromellitic acid. The pyromellitic dianhydride by the method contains little pyromellitic monoanhydride and other monoanhydrides derived from impurities and is less discolored. The pyromellitic dianhydride has particle properties not causing plugging, etc. during its transportation, storage and use.

12 Claims, No Drawings

PRODUCTION METHOD OF HIGHLY PURE PYROMELLITIC DIANHYDRIDE

BACKGROUND OF THE INVENTION

1. Field of the Invention

The present invention relates to a production method of highly pure pyromellitic dianhydride which is used as materials for highly heat-resistant polyimide resins, cross-linking agents for foamed polyesters, specialty plasticizers, etc.

2. Description of the Prior Art

Pyromellitic acid is known to be produced by the liquid-phase oxidation of durene and the liquid-phase oxidation of 2,4,5-trimethylbenzaldehyde, etc. It has been also known that the crude pyromellitic acid obtained in these methods can be converted into pyromellitic dianhydride by the anhydrization in the presence of an aliphatic acid anhydride such as acetic anhydride (for example, Japanese Patent 2515296). The method proposed in the patent requires two mole of acetic anhydride per one mole of pyromellitic acid and necessitates an additional treatment of by-produced acetic acid, increasing the production costs. In another method, pyromellitic acid is converted into pyromellitic dianhydride by the dehydration under heating at limited temperatures (for example, JP 62-59280A). This method is disadvantageous because of its difficulty in controlling the particle properties and preventing the discoloration of pyromellitic dianhydride. Also known is a vapor-phase oxidation of durene or 2,4,5-trimethylbenzaldehyde (for example, JP 2000-1484A). The pyromellitic dianhydride produced by this method contains a small amount of by-produced monoanhydrides such as trimellitic anhydride. Such monoanhydrides should be removed as completely as possible, because they act as the polymerization inhibitor of pyromellitic dianhydride and diamine for the production of polyimide resins. JP 2001-59022A proposes linear or acicular particles of pyromellitic dianhydride having an angle of repose of 50 to 70°, which is used to increase the molecular weight of thermoplastic resins. However, these techniques cannot control the particle size of pyromellitic dianhydride particles, and the proposed pyromellitic dianhydride particles cause problems of plugging, etc. in industrial use because of their high angle of repose.

The crude pyromellitic acid generally contains impurities such as by-product of oxidation reaction and intermediate compounds. Of such impurities, aromatic dicarboxylic acids such as phthalic acid and aromatic tricarboxylic acids such as trimellitic acid and methyltrimellitic acid, which are converted into monoanhydrides simultaneously with the anhydrization of pyromellitic acid, should be removed as completely as possible. Pyromellitic monoanhydride, which is formed by the incomplete or partial anhydrization of pyromellitic acid, should be also removed as completely as possible. Since the melting point is as extremely high as 287° C., pyromellitic dianhydride is generally used in particle forms. The pyromellitic dianhydride proposed in the above patent documents can cause plugging of pipelines, outlets of silos, inlets of reactors, etc. because of its particle properties. If pyromellitic dianhydride is discolored, thermoplastic resins produced using pyromellitic dianhydride as a raw material or an additive may be also discolored. The above problems can be avoided in some extent by the anhydrization of pyromellitic acid by acetic anhydride under heating. However, an increased amount of acetic anhydride should be required, and additionally, acetic acid and acetic anhydride after use should be removed from the system together with pyromellitic dianhydride dissolved therein to prevent the accumulation of impurities in the system, increasing production costs.

SUMMARY OF THE INVENTION

An object of the present invention is to provide a method of inexpensively producing pyromellitic dianhydride which contains little monoanhydrides such as aromatic dicarboxylic monoanhydrides, aromatic tricarboxylic monoanhydrides and pyromellitic monoanhydride (may be collectively referred to as "aromatic monoanhydride"), which has particle properties not causing plugging of reactors, pipelines, etc., and which is less discolored.

As a result of extensive research, the inventors have found that the above object is achieved by subjecting a crude pyromellitic acid to dehydration under heating in the absence of acetic anhydride, and then, subjection a resultant reaction product to anhydrization under heating in the presence of acetic anhydride. The invention is based on this finding.

Thus, the present invention relates to a method of producing pyromellitic dianhydride which includes a step of subjecting a crude pyromellitic acid to dehydration under heating in the absence of acetic anhydride to convert 50.0 to 99.5% by weight of pyromellitic acid to pyromellitic dianhydride, thereby obtaining a reaction product mixture containing at least pyromellitic acid and pyromellitic dianhydride; and a step of subjecting to the reaction product mixture to anhydrization under heating in the presence of acetic anhydride.

DETAILED DESCRIPTION OF THE INVENTION

The starting crude pyromellitic acid may be a crude pyromellitic acid obtained by the liquid-phase oxidation of durene, 2,4,5-trimethylbenzaldehyde, etc. in the presence of an oxidizing agent such as nitric acid, chromic acid and molecular oxygen in at least on solvent selected from water, aliphatic carboxylic acids and aromatic carboxylic acids; a crude pyromellitic acid obtained by the hydrolysis of pyromellitic anhydride which has been produced by a vapor-phase catalytic oxidation, and a crude pyromellitic acid obtained in any of other methods.

The crude pyromellitic acid obtained by oxidation generally contains impurities, for example, aromatic dicarboxylic acids such as phthalic acid and methylphthalic acid and aromatic tricarboxylic acids such as trimellitic acid, methyltrimellitic acid and methyloltrimellitic acid, particularly trimellitic acid in a relatively larger amount. It is preferred for the production of highly pure pyromellitic dianhydride to purify the crude pyromellitic acid in advance by recrystallization from water. However, the loss during purification increases production costs if trying to purify the crude pyromellitic acid to 99.5% purity or higher.

In the method of the invention, the crude pyromellitic acid is first dehydrated under heating in the absence of acetic anhydride. After removing the generated water from the reaction system, a mixture containing non-reacted pyromellitic acid and pyromellitic dianhydride, or a mixture containing non-reacted pyromellitic acid, pyromellitic dianhydride and pyromellitic monoanhydride is obtained. The heating is preferably made indirectly by a heating medium. Various kinds of heating media are usable, and examples thereof include organic heating media such as Dowtherm, Mobiletherm, Malotherm, diphenyl heating medium, triphenyl heating medium and Therm S and inorganic heating media such as niter, although not limited thereto. Alternatively, the heating may be made by pressurized steam or electric heater.

The apparatus for dehydrating the crude pyromellitic acid under heating may be of any type as far as the solid materials can be uniformly heated, and may be selected from fluidized bed apparatus, fixed bed apparatus, batch-wise apparatus, semi-continuous apparatus and continuous apparatus. For example, the dehydration is performed in a trough dryer or a paddle dryer each being equipped with a jacket and a heating rotor. The dehydration is conducted under atmospheric pressure, applied pressure or reduced pressure, preferably under atmospheric pressure or reduced pressure of 5 to 100 kPa, because the generated water is efficiently removed. During the dehydration under heating, a gas, such as nitrogen and an exhaust gas from oxidation reactor for producing terephthalic acid, isophthalic acid, etc., having an oxygen concentration of preferably 10% by weight or less, more preferably 2% by weight, and still more preferably 0.5% by weight is flowed through the reaction system. The water content of the gas is reduced in advance preferably to 5% by weight or less, more preferably to 1% by weight or less, and still more preferably to 0.1% by weight or less. The flow rate is preferably from 0.1 to 20 Nm$^3$/h and more preferably from 0.5 to 10 Nm$^3$/h (Nm$^3$: gas volume at 0° C. and 101 kPa).

By the dehydration under heating in the absence of acetic anhydride, 50 to 99.5% by weight, preferably 70 to 99.5% by weight and more preferably 90 to 99.5% by weight of the starting pyromellitic acid is converted into pyromellitic dianhydride. If the conversion exceeds 99.5% by weight, the crystals of pyromellitic dianhydride adhere to the inner wall of the reactor to cause discoloration. If the conversion is less than 50% by weight, an increased amount of acetic anhydride is required in the next step of anhydrization to increase production costs. The temperature of dehydration (temperature of heating medium) is preferably from 200 to 270° C. and more preferably from 220 to 270° C. Within the above range, the reaction rate of dehydration under heating is not lowered, and the discoloration and sublimation of the crystals of pyromellitic dianhydride being produced are avoided. The time for the dehydration under heating is preferably from 0.5 to 50 h and more preferably from 1 to 24 h. After completion of the dehydration under heating, the generated water is removed from the reaction system. The aromatic dicarboxylic acids such as phthalic acid and the aromatic tricarboxylic acids such as trimellitic acid contained in the starting crude pyromellitic acid are also removed from the reaction system mainly in the form of monoanhydrides together with the removal of the generated water. The by-produced monoanhydrides of aromatic dicarboxylic acids and aromatic tricarboxylic acids have lower boiling points and higher abilities of sublimation as compared with their free acid forms, thereby easily removed from the reaction system. In the present invention, the content (% by weight) of pyromellitic dianhydride is defined as the remainder which is left after subtraction of the total content of pyromellitic acid, pyromellitic monoanhydride, trimellitic anhydride, methyltrimellitic anhydride, and phthalic anhydride from 100% by weight.

The mixture containing non-reacted pyromellitic acid and pyromellitic dianhydride or mixture containing non-reacted pyromellitic acid, pyromellitic dianhydride and pyromellitic monoanhydride obtained by the dehydration under heating is then subjected to anhydrization under heating in the presence of acetic anhydride, to complete the dianhydrization of pyromellitic acid. The amount of acetic anhydride to be used is 0.1 mol or more, preferably 2 mol or more and more preferably from 2 to 20 mol per one mole of the non-reacted pyromellitic acid in the mixture. Since pyromellitic acid is more soluble in the solvent than pyromellitic dianhydride, the use of only 0.1 mol of acetic anhydride per one mole of the non-reacted pyromellitic acid can provide highly pure pyromellitic dianhydride through the crystallization. To recycle a higher proportion of mother liquor, the use of 2 mol or more is preferred. Although the anhydrization may be performed in the presence of only acetic anhydride, preferably performed in the co-presence of a solvent. Examples of the solvents include aliphatic carboxylic acids such as acetic acid and propionic acid; aromatic hydrocarbons such as toluene, xylene and mesitylene; aliphatic hydrocarbons such as hexane, heptane and cyclohexane; and ethers such as dimethyl ether and tetrahydrofuran, with acetic acid being particularly preferred. Since water, alcohols and amines easily react with pyromellitic dianhydride produced, the amount thereof in the reaction system should be controlled within the range of preferably 1 mol % or less, more preferably 0.5 mol % or less and still more preferably 0.1 mol % or less each based on the amount of pyromellitic dianhydride to be finally produced. The water being eliminated from pyromellitic acid and pyromellitic monoanhydride during the anhydrization under heating reacts with acetic anhydride simultaneously with its elimination. Therefore, the reaction system of the anhydrization under heating contains substantially no eliminated water in its free from, to avoid the loss of the produced pyromellitic dianhydride.

Acetic anhydride or an acetic anhydride/solvent mixture is use in an amount preferably from 1 to 30, more preferably from 2 to 10, and still more preferably from 2.5 to 8 when expressed by an SR ratio (ratio of acetic anhydride or the mixture to the total weight of pyromellitic dianhydride to be finally produced). The content of acetic anhydride in the mixture is preferably from 0.01 to 99% by weight and more preferably from 0.01 to 20% by weight. The anhydrization under heating proceeds in ether state of slurry or complete solution, and is preferably performed in a complete solution or in a state in which 90% by weight or more of the product mixture containing pyromellitic acid, pyromellitic dianhydride and pyromellitic monoanhydride is dissolved in acetic anhydride or the mixture, because the particle size of pyromellitic dianhydride becomes larger. The complete solution is obtained preferably by filtering a solution through a sintered metal or a porous carbon to remove insolubles such as metals.

The anhydrization under heating is performed preferably at 50 to 250° C., more preferably at 80 to 200° C., and still more preferably at 100 to 175° C. The reaction pressure is preferably equal to or higher than the vapor pressure of the solvent at the temperature for performing the anhydrization under heating. The reaction is conducted in any of batch-wise manner, semi batch-wise manner and continuous manner. The reaction time for batch-wise or semi batch-wise reaction is preferably from 0.01 to 30 h and more preferably from 0.1 to 10 h. The residence time for continuous reaction is preferably from 0.02 to 50 h and more preferably from 0.2 to 20 h. When the solvent is used, the concentration of acetic anhydride in the mixture of acetic anhydride, the solvent and acetic acid generated from acetic anhydride after the completion of anhydrization is preferably from 0 to 5% by weight and more preferably from 0 to 3% by weight. By selecting the amount of solvent so as to make the concentration of acetic anhydride within the above range, pyromellitic dianhydride having a larger particle size and being less discolored is obtained.

After the completion of anhydrization, the reaction production solution is cooled to precipitate the crystals of pyromellitic dianhydride. Prior to the crystallization, acetic anhydride, the solvent and acetic acid generated in the anhydrization under heating may be partly removed by vaporization. When the anhydrization is carried out in the state of slurry, the reaction production solution may be cooled also in the state of slurry or after made into a complete solution. The crystallization is performed in any of batch-wise manner, semi batch-wise manner and continuous manner. In the batch-wise or semi batch-wise crystallization, the reaction product solution is cooled preferably to 0 to 90° C., more preferably to 5 to 70° C., and still more preferably to 17 to 60° C. The crystallization in such manners may be carried out in the same vessel used for the anhydrization under heating. In the continuous crystallization, at least one, preferably at least two crystallization vessels are provided in addition to the reaction vessel. By setting the temperature of the first crystallization vessel immediately after the reaction vessel preferably to 85 to 140° C. and more preferably to 90 to 120° C., crystals having a larger particle size can be obtained. It is preferred to set the temperatures of the second and subsequent crystallization vessels so as to gradually decrease toward the last crystallization vessel which is maintained preferably at 0 to 90° C., more preferably at 5 to 70° C., and still more preferably at 17 to 60° C.

The cooling may be performed in any manners which are generally employed in the art. Preferred is a method in which acetic anhydride, solvent and acetic acid formed in the anhydrization under heating are partly vaporized under reduced pressure, and the resultant vapor is cooled by a heat exchanger for reuse in the crystallization system. Alternatively, the cooling by an external heat exchanger or the cooling by a jacketed reactor can be employed. The methods mentioned above may be combined. Apart of the vaporized solvent may be removed from the crystallization system.

By optimizing the cooling rate of the reaction production liquid, the particle size of pyromellitic dianhydride can be regulated within a preferred range. When highly flowable crystals are intended, the cooling rate in the batch-wise or semi batch-wise crystallization is preferably from 5 to 300° C./h and more preferably from 20 to 200° C./h. The cooling rate may be changed or maintained constant within the above range. When keeping the temperature constant within the above range for a given period of time, crystals with larger particle size are obtained in some cases. The total of the residence times in the crystallization vessels of the continuous crystallization is preferably from 0.02 to 50 h and more preferably from 0.2 to 20 h. In particular, the residence time in the crystallization vessel immediately after the reaction vessel is preferably from 0.5 to 10 h. The flowability of crystals increases with increasing number of the crystallization vessels.

In the batch-wise or semi batch-wise crystallization, the flowability of crystals can be increased in come cases by adding seed crystals of pyromellitic dianhydride prior to starting the cooling. The seed crystals are added in an amount not dissolving completely into the solvent at temperatures in the cooling step, preferably from 5 to 50% by weight and more preferably from 5 to 30% by weight each based on the amount of pyromellitic dianhydride to be finally produced.

The slurry of pyromellitic dianhydride after cooling was separated into crystals of pyromellitic dianhydride and mother liquor by a known centrifugal separator such as Young type, basket type, super decanting type, tray filter type, horizontal belt filter type an Escher-Wyss type. The separated crystals may be washed with the solvent mentioned above and/or acetic anhydride, if necessary. The recovered mother liquor and/or washings can be reused in the anhydrization under heating. The whole amount thereof may be reused, and a part thereof may be removed from the system so as to prevent the accumulation of discolored substances and impurities. If removing from the system, the amount to be removed is preferably 30% or less of the mother liquor. From the mother liquor and/or washings removed from the system, pyromellitic dianhydride can be recovered by concentration. It is industrially advantageous to reuse the whole amount thereof in view of production costs. It is preferred to remove acetic acid from the system in an amount corresponding to the amount of acetic acid generated in the anhydrization under heating. The removal of acetic acid from the system can be effected by a known method, for example, by distilling the solvent recovered in the drying step of crystals which will be described below. The removed acetic acid can be used, for example, as a solvent for the oxidation to produce terephthalic acid.

If the separated mother liquor and/or washings contain impurities such as aromatic dicarboxylic acids, aromatic tricarboxylic acids and aromatic monoanhydrides in large amounts, the reuse thereof in the anhydrization under heating causes contamination of pyromellitic dianhydride being produced, to reduce the purity of pyromellitic dianhydride. Such impurities act as a polymerization terminator in the synthesis of polyimide using pyromellitic dianhydride. Particularly, trimellitic acid which is a major impurity of the starting material is converted into trimellitic anhydride in the anhydrization step. Since trimellitic anhydride enters into the mother liquor and is accumulated in the system by reuse, the crystals of pyromellitic dianhydride are unfavorably contaminated, thereby limiting the reuse of the mother liquor. In the present invention, however, the contents of impurities in the mother liquor are reduced by the preceding dehydration under heating in the absence of acetic anhydride, thereby allowing the reuse of increased amount of mother liquor. Therefore, the method of the invention is of industrially great advantage.

The method of the invention provides pyromellitic dianhydride in the form of crystal having a large average particle size. The slurry before the solid-liquid separation may be, if necessary, classified by a cyclone, etc. to remove fine crystals. Then, the slurry thus treated is subject to the solid-liquid separation by a known method. By such treatments, crystals of pyromellitic dianhydride containing little fine crystals and having a larger average particle size can be obtained. Also, by reusing a part of the fine crystals and mother liquor each removed by the classification in the anhydrization under heating, crystals having a large average particle size can be obtained. The fine crystals can be removed also by conducting the solid-liquid separation in a centrifugal separator while controlling the height of weir.

The crystals collected by filtration are dried in a known dryer such as paddle dryer, Nauta mixer, fluidized bed dryer, vacuum agitation dryer and disc dryer preferably until the content of residual solvent is reduced to 0.3% by weight or less. Particularly, the drying is continued until the total content of acetic acid and acetic anhydride is reduced to 0.2% by weight or less, preferably 0.1% by weight or less, and more preferably 0.05% by weight or less. Large amounts of acetic acid and acetic anhydride remaining in the crystals cause problems of generation of unpleasant odor, termination of polymerization reaction, and generation of acetic acid. In case of using a dyer equipped with a mixer or a paddle, the rotation speed is preferably controlled so as to avoid the crush of crystals.

In the method of the invention, the produced crystals of pyromellitic dianhydride have an average particle size of preferably from 160 to 800 μm and more preferably from 180 to 500 μm. The average particle size referred to herein corresponds to the opening of sieve on which 50% by weight of crystals remains not passing through (50% onsieve), and is calculated from the particle size distribution determined by the classification using standard sieves. The ratio W/D, wherein D is the average particle size and W is the difference between the opening of 15.9% onsieve and the opening of 84.9% onsieve corresponding to the width of particle size distribution, is preferably from 1.2 to 1.8. The content of crystals having particle sizes of less than 106 μm is preferably less than 15% by weight.

Pyromellitic dianhydride crystals having an excessively large particle size can be, if necessary, crushed by a known crusher or removed by a sieving machine.

The angle of repose of pyromellitic dianhydride produced by the method of the invention is preferably 49° or less, and the balk density thereof is preferably from 0.7 to 1.4 g/cc. With such crystalline properties, pyromellitic dianhydride produced by the method of invention causes no plugging of pipelines, outlets of silos, inlets of reactors, and can be advantageously used in industrial processes in the form of powder. In addition, since the crystals of pyromellitic dianhydride are hard and impact-resistant, the crystals are hardly finely ground by the impact being applied during transportation.

In the method of the invention, since the discolored substances enter into the mother liquor, pyromellitic dianhydride is less discolored. Therefore, the methanol solution color of pyromellitic dianhydride which will be described below is as low as 5 or less. Even when the purity of the starting pyromellitic acid is low because of organic impurities such as phthalic acid and trimellitic acid, pyromellitic dianhydride containing little organic impurities is produced in the present invention by first subjecting the starting crude pyromellitic acid to dehydration under heating in the absence of acetic anhydride, then subjecting to the anhydrization under heating in the presence of acetic anhydride, and then crystallizing pyromellitic dianhydride from a solution. The contents of metals and halogens can be also reduced. The content of aromatic monoanhydrides in pyromellitic dianhydride produced in the present invention is reduced to preferably 2000 ppm or less and more preferably 1000 ppm or less. Particularly, the content of trimellitic anhydride, which is derived from trimellitic acid in the starting pyromellitic acid and can act as a polymerization terminator, is reduced to preferably 1000 ppm or less and more preferably 500 ppm or less. By polymerizing the pyromellitic dianhydride produced in the present invention with diamines or diols, polymers having a sufficiently high degree of polymerization can be produced.

According to the method of the invention, pyromellitic dianhydride, which contains little aromatic monoanhydrides, little causes the plugging of pipelines and is little discolored, is stably produced at reduced costs. Therefore, the present invention is of great industrial value.

The present invention will be explained in more detail by reference to the following examples which should not be construed to limit the scope of the present invention thereto. In the examples and comparative examples below, each measurement was conducted by the following method.

(1) Contents of aromatic monoanhydrides (trimellitic anhydride, methyltrimellitic anhydride and phthalic anhydride) and pyromellitic acid after dehydration under heating An amount of sample was dissolved in acetone-d6 manufactured by Merck & Co., Inc. The resultant solution was analyzed by FT-NMR "JNM-AL-400" available from JEOL, Ltd. The content (% by weight) was calculated from the area of each peak attributable to the aromatic protons of aromatic monoanhydrides, or the aromatic protons of pyromellitic acid.

(2) Contents of pyromellitic acid, trimellitic acid, methyltrimellitic acid, and phthalic acid (Reference Example)

A sample was subjected to esterification in methanol/$BF_3$. Each ester was analyzed by a gas chromatograph "HP6890" available from Hewlett-Packard Company.

(3) Contents of pyromellitic dianhydride, trimellitic anhydride, methyltrimellitic anhydride, and phthalic anhydride A sample was subjected to esterification in methanol/$BF_3$. Then, the contents of pyromellitic acid, pyromellitic monoanhydride, trimellitic anhydride, methyltrimellitic anhydride, and phthalic anhydride were determined by a gas chromatographic analysis using "HP6890" available from Hewlett-Packard Company. The content of pyromellitic dianhydride was calculated by the subtraction of these contents from 100% by weight.

(4) Content of acetic acid in pyromellitic dianhydride

An amount of sample was dissolved in acetone-d6 manufactured by Merck & Co., Inc. The resultant solution was analyzed by FT-NMR "JNM-AL-400" available from JEOL, Ltd. The content (% by weight) was calculated from the area of the peak attributable to methyl protons of acetic acid.

(5) Particle size distribution

Using the following sieve shaking machine and standard sieves, 30 g of sample was classified. The fraction of each class was calculated from the following equation:

$$\text{Fraction of Class (\% by weight)} = B/A \times 100$$

wherein A is the total weight of sample and B is the weight of sample on each standard sieve.

Sieve shaking machine: Ro-Tap sieve shaking machine available from Tanaka Tec Corporation Standard sieves:

Diameter: 75 mm

Sieve openings: 1000, 500, 250, 180, 125, 106, 90, and 75 μm (6) Average particle size The sieve opening which gave 50% onsieve (average particle size) was calculated from the following equation using the fractions of class determined above:

$$\text{Average particle size} = [(W1-W2) \times (X2-50)]/(X2-X1) + W2$$

wherein:

W1 is the smallest opening (μm) of the standard sieve which gives an oversize cumulative fraction of 50% by weight or less;

W2 is the largest opening (μm) of the standard sieve which gives an oversize cumulative fraction of 50% by weight or more;

X1 is the oversize cumulative fraction (% by weight) of the standard sieve having the opening W1; and X2 is the oversize cumulative fraction (% by weight) of the standard sieve having an opening W2.

The "oversize cumulative fraction" of a given sieve referred to above is a total of the fractions of the classes which have openings equal to or larger than the opening of the given sieve, and means the ratio of the particles having particle sizes which are equal to or larger than the opening of the given sieve on the basis of the total of the particles.

(7) Color

The color of pyromellitic dianhydride was expressed by a methanol solution color. A solution of 5 g of sample in 100 ml of methanol was measured for the absorbance at 432 nm. The value of 100 times the measured absorbance was employed as the methanol solution color.

(8) Angle of repose

Measured using a powder tester "PT-S" manufactured by Hosokawa Micron Corporation.

REFERENCE EXAMPLE

Production of Pyromellitic Acid

Into the first reactor of a continuous two-stage reactor composed of two Zr oxidation reactors each equipped with a reflux condenser, a stirring device, a heating device, an inlet for raw materials, a gas inlet and an outlet for discharging the reaction product, was charged 1000 parts by weight of an aqueous catalyst solution containing 2.3% by weight of bromide ion, 0.44% by weight of manganese ion and 13 ppm of iron ion. Into the second reactor, 500 parts by weight of the aqueous catalyst solution of the same type was charged. The inner pressure was increased to 1 MPa by introducing nitrogen under pressure from the gas inlet. The inner temperature was raised to 210° C. by the heating device.

Into the first reactor, 2,4,5-trimethylbenzaldehyde was supplied at a rate of 90 parts by weight/h, and separately, the aqueous catalyst solution of the same type was supplied at a rate of 780 parts by weight/h. Simultaneously with the beginning of supply of 2,4,5-trimethylbenzaldehyde, the supply of air from the gas inlet was started at a controlled flow rate so as to maintain the oxygen concentration of the exhaust gas from the reactor at 2.5% by weight.

Then, the solution was started to be transferred from the first reactor to the second reactor while maintaining the liquid level of the first reactor at its initial level. At the same time, the supply of an aqueous catalyst solution containing 3.3% by weight of bromide ion, which had been prepared by mixing 58 parts by weight of water and 2 parts by weight of pure hydrogen bromide, into the second reactor was started at a rate of 60 parts by weight/h, and the supply of air from the gas inlet was started at a controlled flow rate so as to maintain the oxygen concentration of the exhaust gas from the second reactor at 4.5% by weight.

Thereafter, the reaction product was discharged from the second reactor at a rate of 150 parts by weight/h, while maintaining the liquid level of the second reactor at its initial level. During the above operations, the inner pressure was kept at 3.2 MPa for the first reactor and at 2.9 MPa for the second reactor.

The reaction product was then hydrogenated at 150° C. under 1 MPa in the presence of a 0.5%-Pd/C catalyst. After cooling, the crystals were separated by filtration and dried. The dried crystals were dissolved in 2.5 times by weight water at 130° C. The solution was cooled to 30° C., and the precipitated crystals were separated, rinsed with the same amount of water and dried at 130° C. for 5 h, to obtain a crude pyromellitic acid (pyromellitic acid: 98.8% by weight; trimellitic acid: 0.6% by weight; methyltrimellitic acid: 0.1% by weight; phthalic acid: 0.2% by weight).

Example 1

Into a trough dryer equipped with a jacket (1 m width, 2 m depth, and 7 m length) and a heating rotor, 3000 kg of the crude pyromellitic acid prepared in Reference Example was charged. A heating medium of 250° C. was passed through the jacket and the rotor while flowing 2 $Nm^3$ of nitrogen through the vapor portion of the dryer and rotating the rotor at 35 rpm. After 8 h of the reaction, the reaction product mixture was obtained, in which the concentration of pyromellitic dianhydride was 97.0% by weight (98% conversion of pyromellitic acid to pyromellitic dianhydride), the concentration of trimellitic anhydride was 0.13% by weight, the concentration of methyltrimellitic anhydride was 0.02% by weight, and the concentration of pyromellitic acid was 2.0% by weight. Phthalic anhydride was not detected.

The mixture thus obtained was made into a slurry by adding an acetic anhydride/acetic acid mixture (60% by weight of acetic anhydride) in an SR ratio of 6.

The anhydrization under heating was allowed to proceed at 120° C. under atmospheric pressure while continuously supplying the slurry to the reaction vessel at a rate corresponding to 0.5-h residence time. The reaction product liquid taken out of the reaction vessel was fed into the first crystallization vessel at a rate corresponding to 1-h residence time while reducing the pressure so as to lower the temperature to 80° C. The liquid from the first crystallization vessel was fed into the second crystallization vessel at a rate corresponding to 1.5-h residence time while reducing the pressure so as to lower the temperature to 35° C. The crystals formed in the second crystallization vessel was separated by a Young filter and the separated crystals were washed with acetic anhydride. After adding fresh acetic acid and acetic anhydride to make up for their consumed amounts, all the mother liquor was recycled into the reaction vessel. The separated crystals were dried in a dryer at 160° C. in a continuous manner at a residence time of 6 h, to obtain pyromellitic dianhydride in 98 mol % yield. The results of measurements on the obtained pyromellitic dianhydride are shown in Table 1. The acetic acid content in pyromellitic dianhydride was 400 ppm. W1 was 500 μm, W2 was 250 μm, X1 was zero, and X2 was 52%.

In a dry box, 10.00 g of 4,4'-diaminodiphenyl ether was dissolved in 60 ml of N-methyl-2-pyrrolidone. After adding 10.89 g of the obtained pyromellitic dianhydride to the solution under stirring, the stirring was continued for one hour. After further adding 0.5 ml of a N-methyl-2-pyrrolidone solution containing 6% by weight of the obtained pyromellitic dianhydride, the stirring was continued for additional 15 min. The polymerization product liquid was measured for the viscosity by a viscometer (BH Type manufactured by Tokyo Keiki Co., Ltd.). The measured viscosity was 420 Pa·s, showing that the degree of polymerization was sufficiently high.

Example 2

The dehydration under heating was performed in the same manner as in Example 1 except for changing the reaction time to 10 h, to obtain a reaction product mixture in which the concentration of pyromellitic dianhydride was 99.0% by weight (99% conversion of pyromellitic acid to pyromellitic dianhydride), the concentration of trimellitic anhydride was 0.12% by weight, the concentration of methyltrimellitic anhydride was 0.02% by weight, and the concentration of pyromellitic acid was 0.6% by weight. Then, the anhydrization under heating was performed in the same manner as in Example 1 except for using an acetic anhydride/acetic acid mixture (10% by weight of acetic anhydride) and supplying the slurry into the reaction vessel at 160° C. under 0.6 MPa, to obtain pyromellitic dianhydride in 98 mol % yield. The results of measurements on the obtained pyromellitic dianhydride are shown in Table 1.

Example 3

The dehydration under heating was performed in the same manner as in Example 1, to obtain a reaction product mixture in which the concentration of pyromellitic dianhydride was 97.0% by weight (98% conversion of pyromellitic acid to pyromellitic dianhydride), the concentration of trimellitic anhydride was 0.13% by weight, the concentration of methyltrimellitic anhydride was 0.02% by weight, and the concentration of pyromellitic acid was 2.0% by weight. Thereafter, the procedure of Example 1 was repeated except for changing the temperature of the first crystallization vessel to 90° C. and the temperature of the second crystallization vessel to 40° C., to obtain pyromellitic dianhydride in 98 mol % yield. The results of measurements on the obtained pyromellitic dianhydride are shown in Table 1.

Example 4

The dehydration under heating was performed in the same manner as in Example 1 except for changing the reaction time to 7.5 h, to obtain a reaction product mixture in which the concentration of pyromellitic dianhydride was 95.0% by weight (96% conversion of pyromellitic acid to pyromellitic dianhydride), the concentration of trimellitic anhydride was 0.13% by weight, the concentration of methyltrimellitic anhydride was 0.02% by weight, and the concentration of pyromellitic acid was 3.9% by weight. The mixture thus obtained was made into a slurry by adding an acetic anhydride/acetic acid mixture (5% by weight of acetic anhydride) in an SR ratio of 5. After feeding the slurry to the reaction vessel, the temperature was raised to 170° C. and kept there for one minute under 0.6 MPa. Then, the temperature was lowered to 40° C. at a rate of 100° C./h. The crystals formed in the slurry was separated by a basket filter and the separated crystals were washed with acetic acid. The concentration of acetic anhydride in the mother liquor was adjusted to 5% by weight by adding fresh acetic acid and acetic anhydride to make up for their consumed amounts. Then, the above procedure was repeated 10 times, to obtain pyromellitic dianhydride in 98 mol % yield. The results of measurements on the obtained pyromellitic dianhydride are shown in Table 1.

Comparative Example 1

The dehydration under heating was performed in the same manner as in Example 1 except for changing the reaction time to 11 h, to obtain a reaction product mixture in which the concentration of pyromellitic dianhydride was 99.5% by weight. Pyromellitic dianhydride was obtained from the mixture in 99 mol % yield. The results of measurements on the obtained pyromellitic dianhydride are shown in Table 1.

Comparative Example 2

The dehydration under heating was performed in the same manner as in Example 1 except for changing the temperature of heating medium to 235° C. and the reaction time to 30 h, to obtain a reaction product mixture in which the concentration of pyromellitic dianhydride was 99.6% by weight. Pyromellitic dianhydride was obtained from the mixture in 99 mol % yield. The results of measurements on the obtained pyromellitic dianhydride are shown in Table 1.

Comparative Example 3

The crude pyromellitic acid obtained in Reference Example was made into a slurry by adding an acetic anhydride/acetic acid mixture (80% by weight of acetic anhydride) in an SR ratio of 6. The anhydrization under heating was allowed to proceed at 120° C. under atmospheric pressure while continuously supplying the slurry to a reaction vessel at a rate corresponding to 3-h residence time.

The reaction product liquid taken out of the reaction vessel was fed into the first crystallization vessel at a rate corresponding to 1-h residence time while reducing the pressure so as to lower the temperature to 80° C. The liquid from the first crystallization vessel was fed into the second crystallization vessel at a rate corresponding to 1.5-h residence time while reducing the pressure so as to lower the temperature to 35° C. The crystals formed in the second crystallization vessel was separated by a Young filter and the separated crystals were washed with acetic anhydride. After removing acetic acid generated in the anhydrization under heating, the mother liquid was added with fresh acetic anhydride to make up for its consumed amount. All the mother liquor was recycled into the reaction vessel. The separated crystals were dried in a dryer at 160° C. in a continuous manner at a residence time of 6 h, to obtain pyromellitic dianhydride in 98 mol % yield. The results of measurements on the obtained pyromellitic dianhydride are shown in Table 1.

In a dry box, 10.00 g of 4,4'-diaminodiphenyl ether was dissolved in 60 ml of N-methyl-2-pyrrolidone. After adding 10.89 g of the obtained pyromellitic dianhydride to the solution under stirring, the stirring was continued for one hour. After further adding 0.5 ml of a N-methyl-2-pyrrolidone solution containing 6% by weight of the obtained pyromellitic dianhydride, the stirring was continued for additional 15 min. The polymerization product liquid was measured for the viscosity by a viscometer (BH Type manufactured by Ibkyo Keiki Co., Ltd.). The measured viscosity was 170 Pa·s, showing that the degree of polymerization was low.

TABLE 1

|  | Examples |  |  |  | Comparative Examples |  |  |
|---|---|---|---|---|---|---|---|
|  | 1 | 2 | 3 | 4 | 1 | 2 | 3 |
| Particle size distribution (% by weight) | | | | | | | |
| 1000 μm or larger | 0.0 | 0.0 | 0.0 | 0.0 | 0.0 | 0.0 | 0.0 |
| 500-1000 μm | 0.0 | 0.0 | 0.9 | 0.9 | 0.0 | 0.0 | 0.5 |
| 250-500 μm | 52.0 | 53.1 | 62.4 | 87.4 | 11.3 | 4.2 | 59.3 |
| 180-250 μm | 39.5 | 38.6 | 34.1 | 9.1 | 22.7 | 21.3 | 37.1 |
| 125-180 μm | 5.1 | 4.9 | 1.5 | 1.5 | 31.5 | 29.1 | 2.0 |
| 106-125 μm | 1.9 | 1.6 | 0.3 | 0.3 | 11.4 | 17.1 | 0.4 |
| 90-106 μm | 0.5 | 1.0 | 0.2 | 0.2 | 5.4 | 8.1 | 0.2 |
| 75-90 μm | 0.4 | 0.4 | 0.2 | 0.2 | 4.5 | 5.1 | 0.2 |
| less than 75 μm | 0.5 | 0.4 | 0.5 | 0.5 | 13.2 | 15.1 | 0.4 |

TABLE 1-continued

|  | Examples | | | | Comparative Examples | | |
| --- | --- | --- | --- | --- | --- | --- | --- |
|  | 1 | 2 | 3 | 4 | 1 | 2 | 3 |
| Average particle size (μm) | 260 | 265 | 303 | 359 | 152 | 134 | 291 |
| angle of repose (°) | 34 | 34 | 33 | 31 | 41 | 44 | 34 |
| Solution color | 3 | 4 | 3 | 2 | 13 | 8 | 4 |
| trimellitic anhydride (wt %) | 0.03 | 0.03 | 0.02 | 0.02 | 0.11 | 0.23 | 0.12 |
| methyltrimellitic anhydride (wt %) | 0.01 | 0.01 | 0.01 | 0.01 | 0.02 | 0.04 | 0.01 |
| pyromellitic monoanhydride (wt %) | 0.01 | 0.01 | 0.01 | 0.01 | 0.02 | 0.04 | 0.01 |
| total monoanhydrides (wt %) | 0.05 | 0.05 | 0.04 | 0.04 | 0.15 | 0.31 | 0.14 |

What is claimed is:

1. A method of producing pyromellitic dianhydride, which comprises a step of subjecting a crude pyromellitic acid to dehydration under heating in the absence of acetic anhydride to convert 50.0 to 99.5% by weight of pyromellitic acid to pyromellitic dianhydride, thereby obtaining a reaction product mixture containing at least pyromellitic acid and pyromellitic dianhydride; and a step of subjecting to the reaction product mixture to anhydrization under heating in the presence of acetic anhydride.

2. The method according to claim 1, wherein the anhydrization under heating is performed in the presence of acetic anhydride or an acetic anhydride/solvent mixture in an amount of 1 to 30 parts by weight per one part by weight of pyromellitic dianhydride to be finally produced.

3. The method according to claim 1, wherein the anhydrization under heating is performed in acetic anhydride or an acetic anhydride/solvent mixture in the presence of acetic anhydride in an amount of 2 mol or more per one mol of non-reacted pyromellitic acid.

4. The method according to claim 1, wherein the anhydrization under heating is performed in an acetic anhydride/solvent mixture such that a concentration of acetic anhydride in a mixture of acetic anhydride, the solvent and acetic acid generated from acetic anhydride after completion of the anhydrization under heating is 0 to 5% by weight.

5. The method according to claim 1, wherein a reaction product mixture after the anhydrization under heating is cooled to allow pyromellitic dianhydride to crystallize.

6. The method according to claim 1, wherein the crude pyromellitic acid contains aromatic dicarboxylic acid and/or aromatic tricarboxylic acid.

7. The method according to claim 1, wherein a concentration of aromatic monoanhydride in pyromellitic dianhydride is 2000 ppm or less.

8. The method according to claim 1, wherein a concentration of trimellitic anhydride in pyromellitic dianhydride is 1000 ppm or less.

9. The method according to claim 1, wherein an average particle size of crystals of pyromellitic dianhydride is 160 to 800 μm.

10. The method according to claim 1, wherein a content of crystals having a particle size of less than 106 μm in pyromellitic dianhydride is less than 15% by weight.

11. The method according to claim 1, wherein an angle of rest of crystals of pyromellitic dianhydride is 49° or less.

12. The method according to claim 1, a methanol solution color of pyromellitic dianhydride is 5 or less.

* * * * *